(12) United States Patent
Bowman et al.

(10) Patent No.: US 6,632,183 B2
(45) Date of Patent: Oct. 14, 2003

(54) PERFUSION SENSITIVE BIOPSY EXTRACTOR

(75) Inventors: Harry Frederick Bowman, Needham, MA (US); Gregory T. Martin, Cambridge, MA (US)

(73) Assignee: Thermal Technologies, Inc., Cambridge, MA (US)

(*) Notice: Subject to any disclaimer, the term of this patent is extended or adjusted under 35 U.S.C. 154(b) by 143 days.

(21) Appl. No.: 09/783,915

(22) Filed: Feb. 12, 2001

(65) Prior Publication Data

US 2002/0128570 A1 Sep. 12, 2002

(51) Int. Cl.[7] .............................................. A61B 10/00
(52) U.S. Cl. ...................... 600/564; 600/567; 600/504; 600/363; 606/167
(58) Field of Search .................. 600/310, 345, 600/363, 431, 433–435, 453, 454, 465, 468, 504, 562, 564–567, 549; 606/167, 170, 27–31; 604/19, 22, 164.01, 164.11; 374/44

(56) References Cited

U.S. PATENT DOCUMENTS

| 4,059,982 | A |   | 11/1977 | Bowman |
| 4,249,539 | A |   | 2/1981  | Vilkomerson et al. |
| 4,445,515 | A |   | 5/1984  | DiResta |
| 4,681,103 | A |   | 7/1987  | Boner et al. |
| 4,852,027 | A |   | 7/1989  | Bowman et al. |
| 4,971,068 | A | * | 11/1990 | Sahi ........................... 374/147 |
| 5,267,569 | A | * | 12/1993 | Lienhard ................... 324/71.1 |
| 5,320,101 | A |   | 6/1994  | Faupel et al. |
| 5,320,111 | A |   | 6/1994  | Livingston |
| 5,383,465 | A |   | 1/1995  | Lesny et al. |
| 5,579,774 | A | * | 12/1996 | Miller et al. ................. 600/479 |
| 5,769,791 | A |   | 6/1998  | Benaron et al. |
| 5,769,795 | A |   | 6/1998  | Terwilliger |
| 5,782,764 | A |   | 7/1998  | Werne |
| 5,810,010 | A | * | 9/1998  | Anbar ........................ 600/407 |
| 5,980,469 | A | * | 11/1999 | Burbank et al. ............ 600/567 |
| 6,109,270 | A | * | 8/2000  | Mah et al. .................. 128/924 |
| 6,142,955 | A | * | 11/2000 | Farascioni et al. .......... 600/562 |

* cited by examiner

Primary Examiner—Charles A. Marmor, II
(74) Attorney, Agent, or Firm—James A. Neal

(57) ABSTRACT

A technique for quantifying perfusion and removing a biopsy sample at a site in a living body wherein an instrument having a perfusion sensor is introduced into the body at a site to be investigated to there interrogate the tissue. The biopsy specimen is collected when the perfusion sensor produces a signal indicative of perfused, viable tissue.

16 Claims, 4 Drawing Sheets

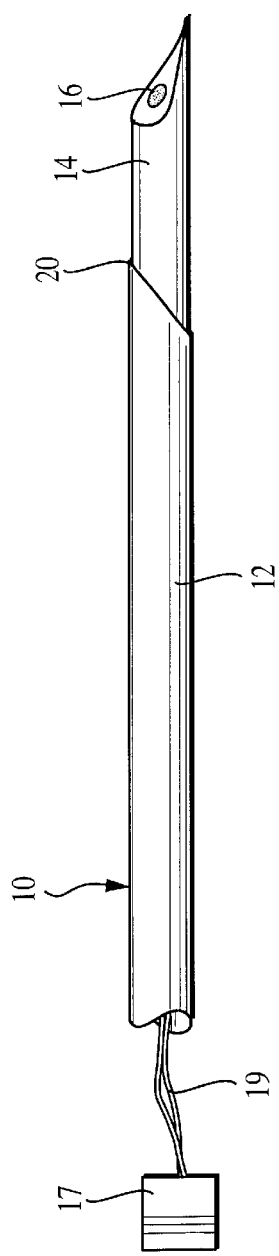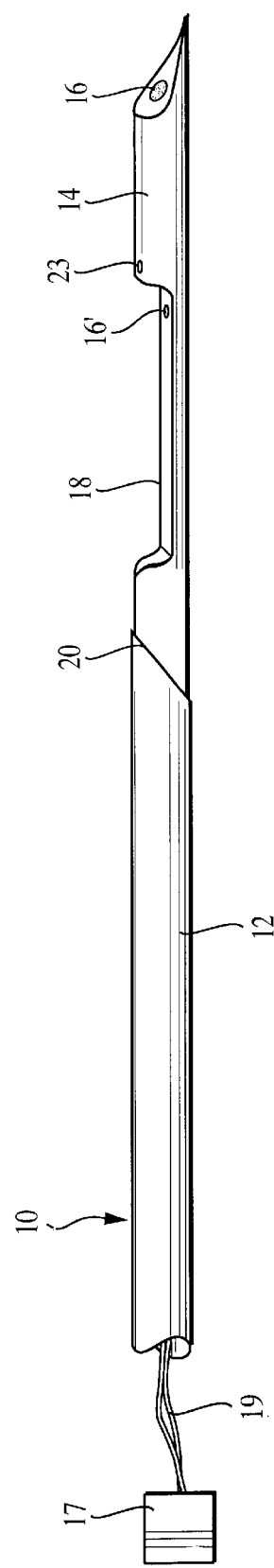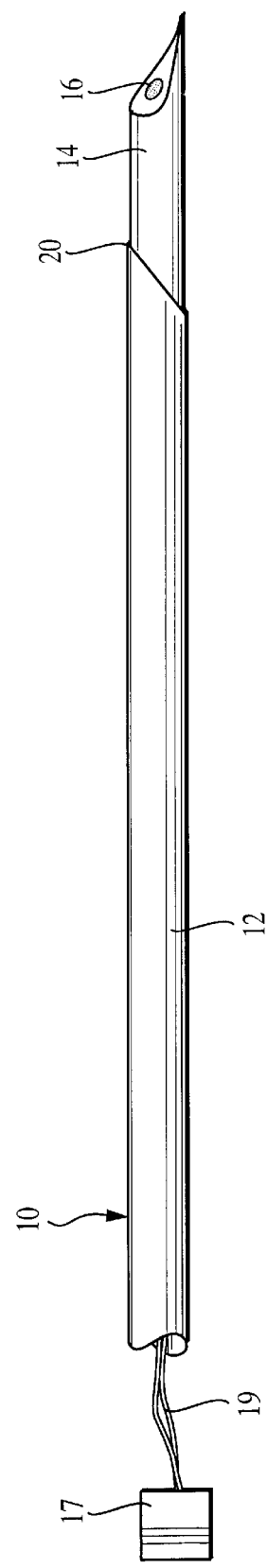

FIG. 4A
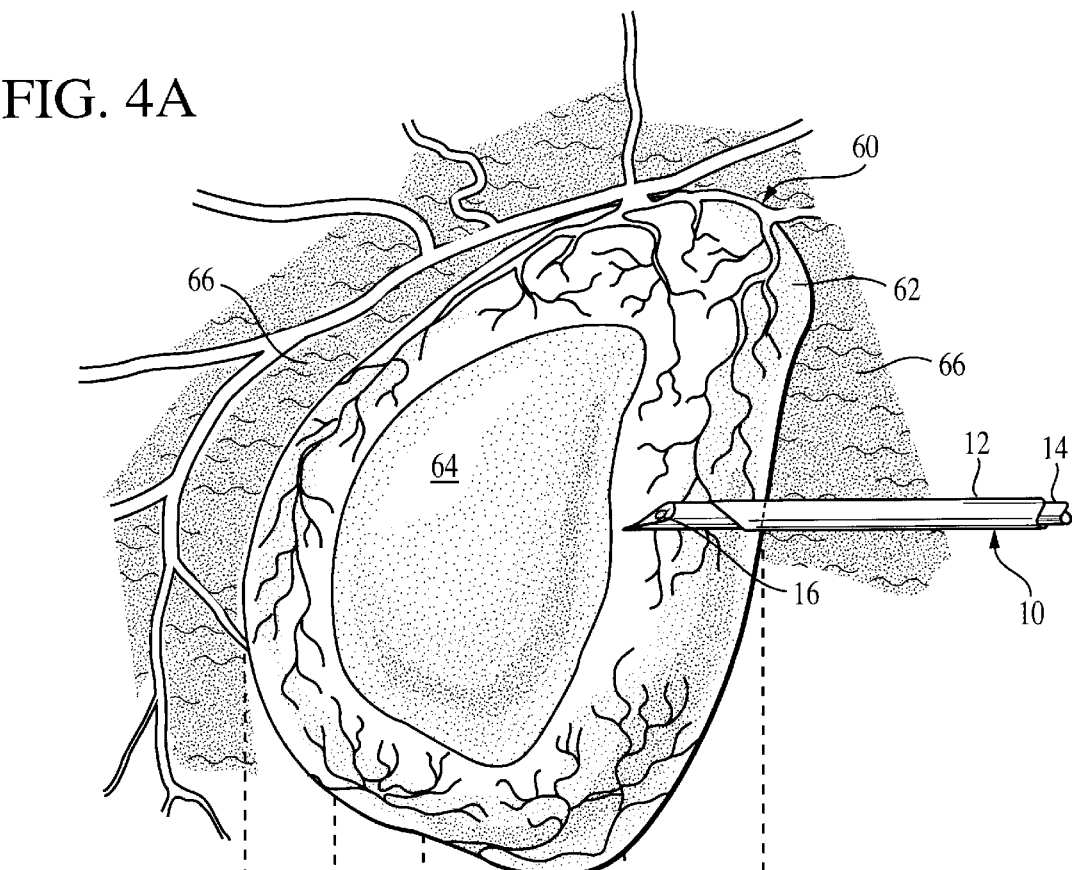
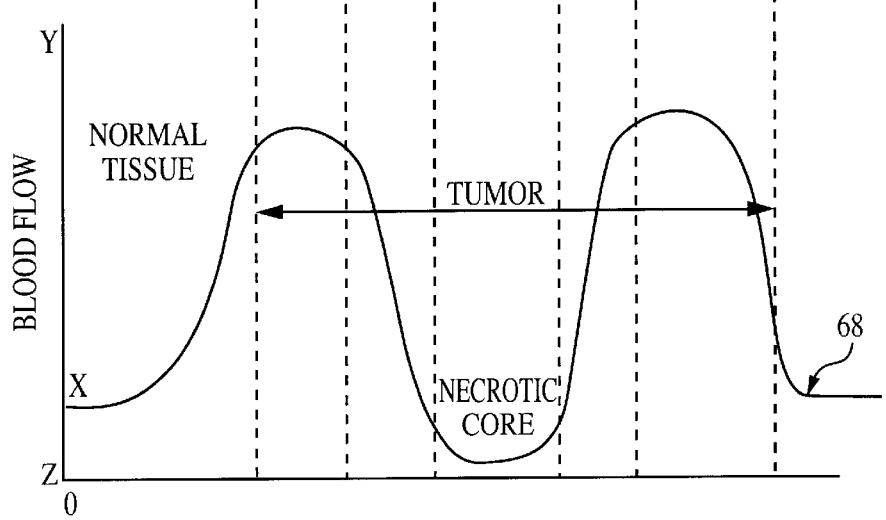
FIG. 4B

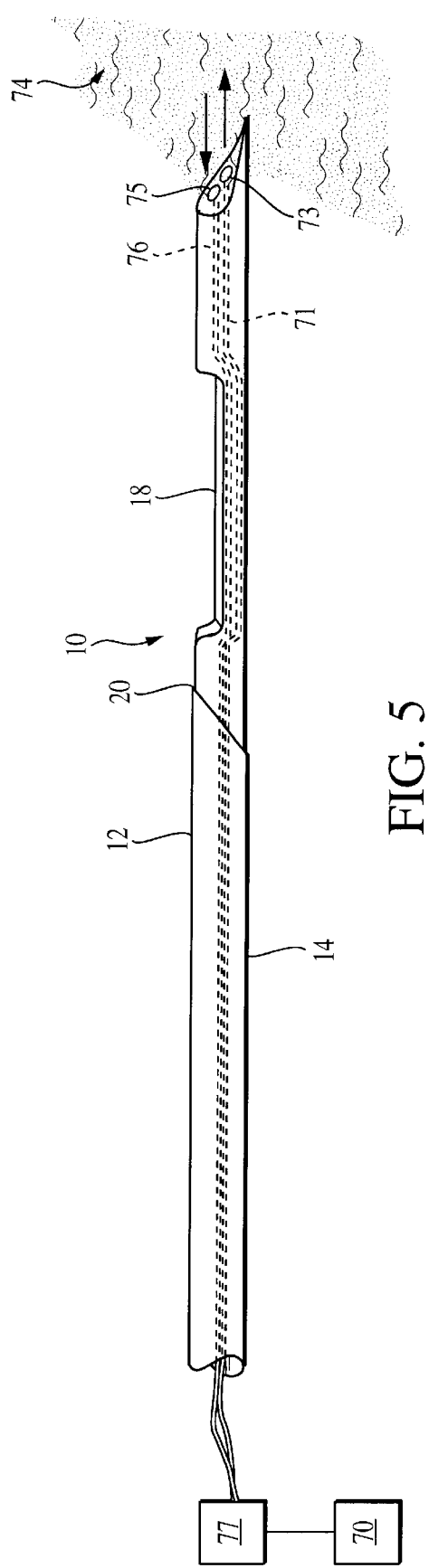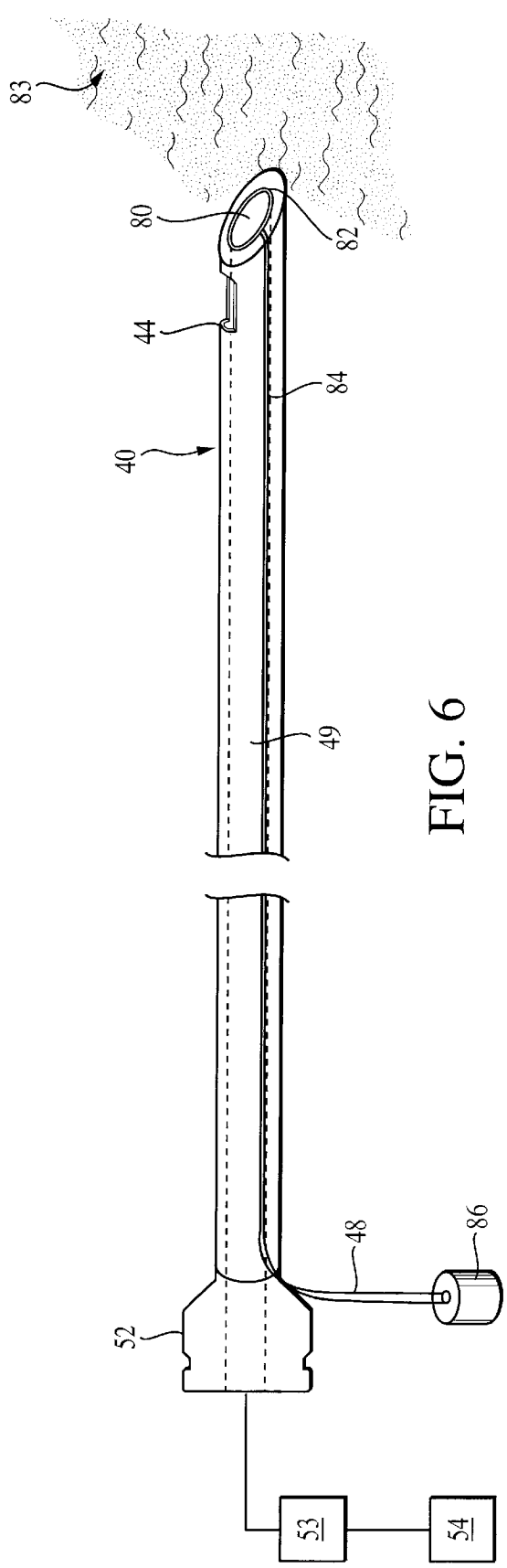

PERFUSION SENSITIVE BIOPSY EXTRACTOR

BACKGROUND OF THE INVENTION

This invention relates to a method and apparatus for quantifying blood flow in tissue and specifically for quantifying blood flow in tissue at a location within the body where therapy or diagnosis is required. The ability to quantify tissue blood flow permits the physician to plan and schedule specific therapies designed for a patient's particular condition. For example, blood flow is a carrier of therapeutic agents throughout the body. The ability to quantify blood flow at a site within the body where drug therapy is required will permit the physician to evaluate the extent to which therapeutic agents introduced into the circulatory system will actually reach and affect the site to be treated.

One clinical area in which the current invention is useful is in the treatment of cancer, particularly those cancer cases that are treated non-surgically. Almost all cancers treated non-surgically will undergo therapies whose efficacy is strongly related to tissue and tumor blood flow. A number of anti-cancer agents depend on the circulatory system for delivery to the target tissue. Blood flow, the carrier of therapeutic agents to the tumor, also acts as a carrier of oxygen. Increased blood supply increases tissue oxygenation and the concentration of chemotherapeutic agents. Correspondingly, the concentration of oxygen at the site and the concentration of chemotherapeutic agents are enhancers of the effectiveness of therapies such as radiation therapy and chemotherapy.

In the treatment of tumors, various techniques have been used to increase the blood flow and thereby increase the oxygen supply to the site in the tumor being treated. Efforts to increase blood flow to tumors include the use of vasoactive drugs, viscosity modifiers and local hyperthermia therapy. In these attempts, circulation is affected systemically but there is always a question of the extent to which circulation in the specific site to be treated is affected. The need to increase blood flow to diseased tissue is associated with a corresponding need to measure or quantify blood flow at the treatment site.

SUMMARY OF THE INVENTION

While the overall importance of blood flow to human health has long been recognized, techniques to quantify blood flow generally have not lent themselves to routine clinical application. Accordingly, it is a purpose of this invention to provide a method and apparatus that will measure blood flow at a specific location critical to patient treatment and permit convenient, routine clinical application.

Certain patient therapies involve the extraction for testing of a tissue sample or biopsy from a region of the body suspected of disease or known to be diseased. The extracted sample is examined to obtain a diagnosis or to assess treatment and, if the tissue is diseased, a treatment protocol is established. It is advantageous to determine the blood perfusion of tissue at the location of the biopsy (i.e.: at the site to be treated) so that the treatment protocol can be based on actual blood flow to the site. The device of this invention is useful in any clinical situation for which perfusion is of interest when a biopsy is being taken. Such situations include eschemic disease and organ failures such as kidney or liver failure. A typical cancer therapy protocol involves the treatment of diseased tissue by chemotherapy, hyperthermia and/or radiation, all of which are, in part, dependent on blood flow. In some cases the perfusion data is used to distinguish viable tissue from necrotic tissue. In other cases there may be within viable tissue a range of perfusion values which may guide the choice of the biopsy site.

In cancer cases the efficacy of almost all non-surgical therapies is strongly related to tissue and tumor blood flow. Blood flow is the carrier of chemotherapeutic agents to the tumor, the carrier of oxygen which contributes to the efficiency of oxic anti-cancer drugs, the primary mechanism of heat removal from tissue in hyperthermic treatment of tumors and the principal modulator of oxygenation which contributes to the effectiveness of radiotherapy. The level of blood flow in a tumor is thought to correlate with probable therapy outcome. This allows individual planning of patient therapy strategies based on the basal level of tumor blood flow and the response to blood flow modifying agents.

The technique of the present invention involves a minimally invasive system for producing a signal characteristic of blood perfusion, measuring blood perfusion in tissue at a selected tissue biopsy site, and obtaining a biopsy sample at or near the site where blood perfusion is measured. Preferred embodiments include a signal producing device that introduces into tissue a signal producing agent and a system for receiving and processing a signal resulting from the action of the signal producing agent in the tissue.

One perfusion monitor using a thermal transducer based perfusion sensor and useful in the practice of this invention is disclosed in U.S. Pat. No. 4,852,027 issued to H. Frederick Bowman et al. Monitors with other perfusion sensors can be used, for example monitors with laser Doppler sensors, hydrogen clearance sensors or ultrasound. The perfusion sensor is mounted on a biopsy needle or other biopsy extraction probe so that tissue samples are taken from the region interrogated by the perfusion sensor. When the instrument is operated the extraction probe is inserted into the tissue to be interrogated, perfusion data is taken and then the probe is operated to extract a sample of the tissue interrogated by the perfusion sensor. In this manner perfusion data taken relates directly to the tissue extracted. The physician is not required to rely upon a generalized systematic tissue perfusion value for the patient from which perfusion at the site of the biopsy is inferred.

The instrument of this invention enables the physician to extract a biopsy sample and measure perfusion simultaneously in one procedure. The tissue forming the biopsy sample is tissue interrogated by the perfusion measurement device. The biopsy sample is extracted from tissue known to be perfused. Tissue perfusion is a strong (typically conclusive) indicator of tissue viability. Thus, the patient (or site) pathology can be determined from the extracted biopsy sample. This eliminates the need for two or multiple invasive procedures in order to obtain a perfused (i.e.: viable) biopsy sample, thus saving patient trauma and time.

The present invention provides: quantification of tissue perfusion to assist in formulating patient specific treatment strategies; the ability to augment the perfusion of specific tissue with blood flow modifying agents and to quantify the augmented perfusion; direct correlation of local tissue perfusion with histological analysis; the knowledge that tissue biopsy is being taken from non-necrotic tissue; and minimization of the number of biopsy probe insertions, thereby minimizing tissue trauma during the biopsy process. Further, because apparent or measured tissue perfusion is higher in tissue which comprehends major blood vessels within the interrogation volume, the device of this invention can be used to detect proximity to major vessels as the probe is being inserted to enable the practitioner to navigate a path through tissue which avoids unwanted puncture of blood vessels.

BRIEF DESCRIPTION OF THE DRAWINGS

A more complete understanding of the present invention will be had from the following description, claims and drawings in which:

FIG. 1A shows an embodiment of the biopsy needle in a first position;

FIG. 1B shows the embodiment of FIG. 1A in a second position;

FIG. 1C shows the embodiment of FIG. 1A in a third position;

FIG. 4A illustrates a tumor being interrogated by a biopsy needle of this invention;

FIG. 4B shows an exemplary blood perfusion pattern in the tumor illustrated in FIG. 4A;

FIG. 5 illustrates a further embodiment of the invention; and

FIG. 6 illustrates a still further embodiment of the invention.

DESCRIPTION OF THE PREFERRED EMBODIMENTS

Figure 2:
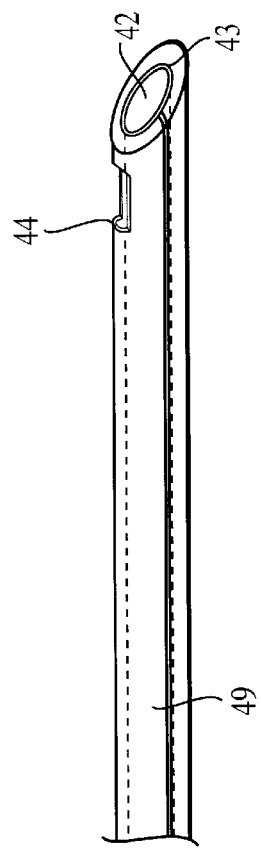
FIG. 2 illustrates an alternate embodiment of the invention.

A core biopsy needle or probe 10 constructed in accordance with the present invention is shown in three different positions in three schematic diagrams, FIG. 1A, FIG. 1B and FIG. 1C. In FIG. 1A, the core biopsy needle 10 includes a cannula 12 defining a sharp cutting edge or blade 20 along its leading edge and an obturator 14 mounted within the cannula 12. The obturator (a notched trocar) and the cannula slide with respect to each other in telescoping or reciprocal fashion. Perfusion sensor 16, which in this embodiment may be in the form of a thermistor, is mounted in the tip of the obturator 14. FIG. 1B shows the core biopsy needle 10 of FIG. 1A with the obturator 14 extended to reveal specimen notch 18. The notch 18 is located on the obturator 14 so as to be in a trailing position relative to the sensor 16 when the obturator 14 is advanced. FIG. 1C shows the core biopsy needle 10 in a further extended position in which the cannula 12 has been advanced to a forward position relative to the obturator 14 covering specimen notch 18. It will be apparent that the obturator and cannula could also be configured for rotary motion relative to each other.

Optionally, a baseline sensor or thermistor 23 can be mounted on the obturator 14 (or the cannula 12) back from perfusion sensor 16 to monitor and compensate for baseline temperature changes. The perfusion sensor 16 and the optional thermistor 23 may be connected to a data processor 17 by lead wires 19 extending through a lumen in the obturator 14.

Referring again to FIG. 1A, the needle 10 is inserted into tissue of a subject to place the tip of the obturator 14 and the thermistor based perfusion sensor 16 in tissue at a potential specimen site. Tissue 22 and included capillaries form a perfused capillary bed surrounding the perfusion sensor 16. (Refer to FIG. 3.) The perfusion sensor 16 is heated to introduce or transmit thermal energy into surrounding tissue 22 and produce a heated field within the tissue. The heated field defines an interrogation volume and an effective measurement zone or field. The perfusion sensor 16 produces a signal proportional to the rate at which thermal energy introduced into the tissue is transported within the tissue. The thermal energy transport (or transfer) rate is a function of the blood flow or perfusion through the tissue. The sensor 16 (thermally based or otherwise) provides a signal, at least one characteristic of which is a function of the perfusion within the interrogation volume and, inferentially, within the effective measurement field. That is, the signal varies with perfusion in the surrounding tissue. The perfusion in tissue in immediate contact with the perfusion sensor 16 has the greatest effect and the effect of perfusion on the sensor decreases as distance from the sensor increases. One explanation of this relationship is given in U.S. Pat. No. 4,059,982 to Bowman.

Figure 3:
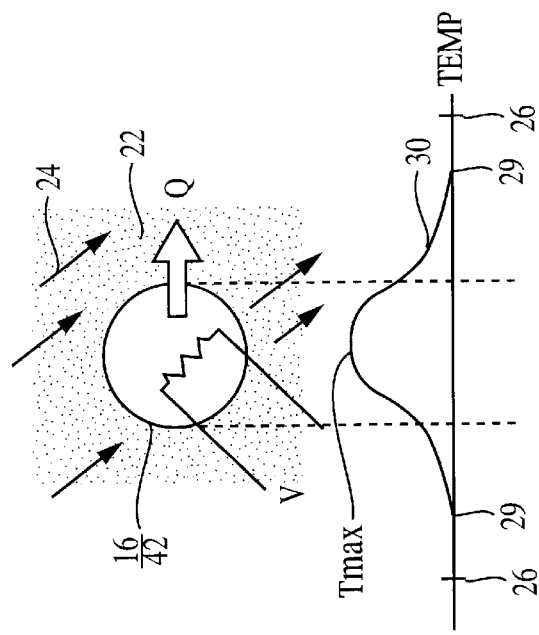
FIG. 3 illustrates the interrogation range of a sensor in a biopsy needle.

In FIG. 3, the direct interrogation volume associated with the sensor 16 is indicated at 29. (That is, the boundary 29 represents the outermost region beyond which a perfusion signal is below the direct detection limit of perfusion sensor 16.) Within a larger zone indicated by boundary 26 the perfusion may be inferred as equivalent to that at the sensor 16. In organs or tissues where the perfusion is known to be spatially homogeneous, a measurement at one site can be used to infer a perfusion value at another site in the same organ or tissue. For instance, perfusion in the white matter of the brain is well known under conditions of normal physiology, to be spatially uniform. Also perfusion in the gray matter of the brain, though different from the white matter, is also known to be uniform. Therefore a perfusion measurement taken at one site in either the gray or white matter, can be used to infer the perfusion value at another site in the gray or white matter, respectively. This is the case even when, within an organ known to be characterized by spatially homogeneous perfusion under normal physiology, there is no physical overlap of the biopsy sample with the direct interrogation volume of the perfusion sensor. Homogeneous perfusion can also be found in other tissue under conditions of normal physiology, such as in cardiac tissue, skeletal muscle, and liver. In operation, the perfusion sensor or thermistor 16 is introduced into tissue 22 (which may be muscle tissue or the tissue of an organ such as the brain, heart or liver) and heated to raise the temperature of the tissue above its reference temperature. Perfusion or flow through the tissue, indicated by arrows 24, causes convective heat transfer from the embedded thermistor to tissue 22. Heat transfer from the thermistor to the tissue increases as flow through the tissue increases. The temperature distribution in the tissue 22 is represented by the curve 30 wherein the maximum temperature occurs at the thermistor 16 and decreases in all directions therefrom, eventually decaying to the temperature of the surrounding tissue, as indicated at 29. The boundary 29 therefore represents the direct detection limit of the perfusion sensor 16. The effective measurement field indicated at 26 is the practical limit within which perfusion is characteristic of or equivalent to that at the perfusion sensor 16, whether due to homogeneous perfusion within an organ being interrogated or otherwise.

The location of the perfusion sensor 16 defines the center of the effective measurement field 26. The site from which the biopsy is taken is to be at least partially within the effective measurement field 26 and, under optimum conditions, the biopsy sample is taken from the same location as the perfusion measurement (i.e.: within the direct interrogation zone 29 of the perfusion sensor 16). Further, tissue near the tip of the biopsy needle where the perfusion sensor 16 is located is the least damaged of any tissue that comes in contact with the biopsy needle. Thus the perfusion measurement at this location is minimally disturbed by the insertion process.

The embodiment of the invention shown in FIG. 1A, FIG. 1B and FIG. 1C is adapted to collect a solid tissue sample from a particular location or selected organ of the body of the subject. That is, this embodiment is adapted to collect aggregated cells at a specific location within the body or within an organ of the body. The biopsy needle 10 is introduced into the subject to locate the tip of the obturator 14 and the perfusion sensor 16 in a selected organ or specimen site. Perfusion data is then taken in the specimen site by the perfusion sensor 16 and processed by data processor 17. When the sensor 16 produces a signal indicative of a perfusion value within a biological or clinical range which corresponds to viable tissue and an appropriate specimen site, the obturator 14 is extended so that, optimally, the specimen notch 18 appears in the same location where the perfusion reading was taken. The same solid tissue in which the perfusion reading was taken fills the specimen notch 18 and constitutes the specimen sample. The cannula 12 is then advanced to cover the specimen notch 18 so the cutting edge 20 severs the specimen sample from the surrounding tissue and confines it between the surface of the specimen notch 18 and the inner surface of cannula 12. The biopsy needle 10 is then withdrawn from the subject with tissue 22 in which the perfusion reading was taken constituting the biopsy sample.

In one embodiment incorporating the baseline sensor 23, the thermistor 16 is heated to a small increment (for example ~2° C.) above the tissue baseline temperature while the sensor 23 monitors baseline temperature fluctuations. The power dissipated by the heated thermistor 16 provides a measure of the ability of the tissue to carry heat and the quantification of tissue blood flow. Data from baseline sensor 23 and thermistor 16 is transmitted to the data processor 17. The data processor quantifies tissue blood flow using data from thermistor 16 and compensates for baseline temperature fluctuations using data from sensor 23. A discussion of the baseline sensor is described by G. T. Martin and H. F. Bowman in "Validation of Real Time Continuous Perfusion Measurement", Medical & Biological Engineering & Computing, Med. Biol. Eng. Comput., 2000, 38, pp 319–325.

The biological or clinical range of perfusion values that corresponds to an appropriate specimen site differs from one location in the body to another. For example, in the white matter of the brain perfusion in normal tissue is 25–50 ml/min/100 g of tissue. In a normal liver it is 70–90 ml/min/100 g of tissue. In oncology, a normal perfusion value may be suggestive of treatment by radiation. A lower perfusion value is consistent with a tumor resistant to treatment by radiation and suggestive of other treatments. Similarly, in organ transplantation, an organ perfusion value lower than normal is indicative of difficulty due to inadequate perfusion and correspondingly inadequate oxygenation.

It will be appreciated that in an alternate embodiment sensor 16' (an alternate to sensor 16) can be located adjacent or within the specimen notch 18. In this case the obturator 14 is first extended so the tissue specimen enters the notch 18. Perfusion data is then taken. After perfusion data is taken, the cannula 12 is advanced to sever the specimen tissue from surrounding tissue. The perfusion data and the specimen are thus taken in the same location.

FIGS. 4A and 4B illustrate a typical blood perfusion pattern in a tumor 60 and surrounding healthy tissue 66. It is common for certain kinds of tumors to consist of a viable growing margin 62 characterized by abnormally high perfusion in comparison to the surrounding healthy tissue 66 and an inner necrotic core 64 where perfusion can reach substantially zero. In FIG. 4B, curve 68 indicates a blood perfusion value "X" for normal tissue 66 and a maximum perfusion value "Y" in the growing margin 62. Minimum perfusion value "Z", which can be substantially zero, occurs in the necrotic core 64. In operation a practitioner might insert the biopsy needle 10 into healthy tissue and find base perfusion readings of the value "X". When the biopsy needle penetrates the growing margin 62 of tumor 60 the perfusion values rise above the base value as indicated by values between "X" and "Y" on the curve 68. This indicates live tumor tissue and an appropriate site for a tumor biopsy. The higher perfusion value indicates an optimum biopsy site. If penetration continues into the necrotic core 64, perfusion values will fall to a value below that of healthy tissue, indicated by values between "X" and "Z" on the curve 68. This indicates dead or necrotic tissue and an inappropriate site for a biopsy.

The embodiment of the invention shown in FIG. 2 is adapted to collect a liquid tissue sample from a particular location or a selected organ of the body of the subject. That is, the biopsy needle 40 is adapted to collect cells suspended in interstitial fluid from a specific location within the body or within an organ of the body. A perfusion sensor 42 is mounted at the leading beveled edge 43 of the biopsy needle 40. The sensor 42 may be a glass encapsulated thermistor in the shape of a probate spheroid set in a lumen opening in the end of the needle 40, at the beveled tip surface of the needle. The sensor 42 may be secured and the end of the lumen in which it is set can be filled with a biocompatible epoxy. Lead wires 48 extended through a lumen 49 in the needle 40 connecting the perfusion sensor 42 to a data processor 50.

Aspiration port 44 is formed in the wall of the needle, in close juxtaposition with perfusion sensor 42, so that, when the biopsy needle 40 is inserted into tissue 22 to position the perfusion sensor 42 at a site from which a biopsy is to be taken, the aspiration port 44 will be located within the effective measurement field 26 defined by the perfusion sensor 42. That is, the aspiration port 44 is located on the biopsy needle to be within the effective measurement field 26 of the perfusion sensor 42. By this configuration, the lumen 49 is in fluid communication with the biopsy specimen site and the effective measurement field 26. Thus, the site from which the biopsy is taken will be at least partially within the effective measurement field 26 established by the perfusion sensor 42 and, in an optimum embodiment, the aspiration port 44 is located to be within the direct interrogation zone 29 of the perfusion sensor 42. Hub 52 connects the lumen 49 to a suitable operating device 53 for creating suction and a liquid tissue sample collector 54. In operation, the biopsy needle 40 is introduced into the subject to locate the perfusion sensor 42 in a selected specimen site. Perfusion values obtained from sensor 42 are processed by data processor 50 as the biopsy needle 40 is being inserted. The perfusion values obtained indicate the appropriate site for a biopsy. With the tip of the needle 40 and perfusion sensor 42 at an appropriate site, the operating device 53, communicating with the biopsy needle through hub 52, aspirates interstitial fluid and liquid tissue from the biopsy site, through the aspiration port 44 and the lumen 49, to the liquid tissue sample collector 54. This tissue constitutes the biopsy sample.

An embodiment of the invention using a laser Doppler sensor technique is illustrated by FIG. 5. Biopsy needle 10 includes cannula 12 and obturator 14 that define specimen notch 18 and blade 20. Laser light from a laser light source 70 is transmitted by a fiber optic channel 71 to transmitting lens 73. Lens 73 focuses and transmits laser light from the fiber optic channel 71 and directs it into tissue 74 surrounding the biopsy needle 10 when the needle is injected into a potential biopsy site in a subject. Laser light from the lens 73 incident upon red blood cells perfusing the surrounding tissue 74 is Doppler shifted and reflected back to receiving sensor or lens 75. This interrogates the surrounding tissue 74. The Doppler shifted light from the surrounding tissue produces a light signal that is transmitted by fiber optic channel 76 to data processor 77. The Doppler shift received by the sensor lens 75 varies with variation in the perfusion (flow) of blood through the surrounding tissue 74. The light signal is converted to an electrical signal in the data processor 77 and is processed. The resulting perfusion value provided by the data processor 77 is based on the perfusion dependent signal from the sensor lens 75 and indicates whether perfusion in the tissue 74 is within a biologically significant range corresponding to an appropriate biopsy site. When at an appropriate biopsy site, the biopsy needle 10 is operated to harvest a biopsy sample in the manner described above in connection with FIG. 1A, FIG. 1B and FIG. 1C.

An embodiment of the invention using a hydrogen sensitive electrode is illustrated by FIG. 6. Biopsy needle or probe 40 defines an aspiration port 44 and a lumen 49 establishing fluid communication between the aspiration port 44 and a suction device 53 and a liquid tissue sample collector 54. Hydrogen sensitive electrode 80 is located at the tip 82 of the probe 40 and electrically communicates by conductors 84 to a data processor 86. When the probe 40 is injected into a potential biopsy site in a subject, the hydrogen sensitive electrode 80 produces an electrical signal which varies as a function of the concentration of hydrogen in blood perfusing the capillary network in the volume of tissue 83 surrounding the electrode 80. The data processor 86 is adapted to process signals from the electrode 80 to provide perfusion values corresponding to the blood perfusion of the capillary network in the volume of tissue 83. In operation the subject breathes a breathable gas including a predetermined concentration of hydrogen, normally substantially above the hydrogen concentration in ambient air. The bloodstream carries the hydrogen throughout the body and introduces hydrogen into bodily tissue. At any given tissue location the hydrogen concentration will increase or decrease, respectively, as the perfusion of that tissue increases or decreases. Further, the rate at which the hydrogen is transferred to or from a tissue site is a function of the perfusion at the site. The hydrogen concentration in the capillary network in the volume of tissue 83 and/or the rate of decay of the hydrogen concentration characterizes the blood perfusion in the capillary network. Electrode 80 produces a signal the magnitude of which is a function of the perfusion of the site. The hydrogen dependent signal from the electrode 80 is fed through conductors 84 to the data processor 86 which provides an output indicative of the perfusion of the capillary network in the volume of tissue 83 and thus of the potential biopsy site. The perfusion value provided by the data processor 86 indicates whether perfusion in the capillary network is within a biologically significant range that corresponds to an appropriate biopsy site. When at an appropriate biopsy site, the Biopsy probe 40 is operated to harvest a biopsy sample in the manner described above in connection with FIG. 2.

During insertion of the needle or probe 10 or 40, the practitioner can monitor perfusion readings to assess proximity of the tip of the needle and the perfusion sensor 16 or 42 to a major blood vessel. The convective heat transfer effective in close proximity to a major blood vessel will cause the system to produce an abnormally high reading (i.e.: above that normally associated with the host tissue). This reading enables the practitioner to guide the insertion to avoid puncturing the blood vessel and to avoid biopsy sites within the thermal influence of the blood vessel. Additionally, data processors can be programmed to respond to a preset threshold perfusion value to signal proximity to a major blood vessel. These signals further enable the practitioner to guide the needle or probe to a site of lower perfusion value and avoid major blood vessels.

The various sensors shown above are shown with particular biopsy needle designs for convenience of description. The sensors illustrated with one needle design can also be used with other needle designs.

What is claimed is:

1. Apparatus for removing a biopsy specimen from a biopsy specimen site in living tissue comprising:

a biopsy probe;

perfusion sensor means on said probe for introducing thermal energy into tissue, thereby defining an effective measurement zone within the tissue, and sensing the transport of said thermal energy within the effective measurement zone; and extraction means on said probe for extracting tissue in the effective measurement zone.

2. Apparatus according to claim 1 further comprising means for compensating for baseline tissue temperature fluctuations.

3. Apparatus according to claim 1 said perfusion sensor means is located on said probe at or near said extraction means so that said extraction means, when in use, is at least partially within said effective measurement zone.

4. Apparatus according to Claim 1 wherein said perfusion sensor means is located at the tip of said probe and at or near said extraction means.

5. Apparatus according to claim 1 wherein said perfusion sensor means is located on said probe adjacent to or within said extraction means.

6. Apparatus according to claim 3, 4 or 5 further comprising:

a sensor for monitoring baseline tissue temperature; and a data processor for calculating perfusion values as a function of data from said perfusion sensor means and said baseline tissue temperature monitoring sensor.

7. A method for removing a perfused biopsy specimen from a biopsy specimen site in a living subject comprising the steps of:

introducing into tissue of the living subject a probe having thereon a specimen collector and a sensor at or near said specimen collector to locate both the sensor and the specimen collector at a biopsy specimen site;

by means of said sensor introducing thermal energy into tissue at the biopsy specimen site;

producing signals characteristic of perfusion in tissue at the biopsy specimen site in response to the transport of thermal energy from said sensor; and operating said specimen collector to withdraw tissue from the biopsy specimen site when the signals resulting from said signal producing step correspond to an appropriate specimen site.

8. A method according to claim 7 further comprising the steps of monitoring baseline temperature fluctuations and compensating for the effect of baseline temperature fluctuations on said signals resulting from said producing step.

9. A method according to claim 8 wherein said introducing step comprises introducing into tissue of the living subject a probe having thereon a specimen collector and a sensor adjacent to or within said specimen collector.

10. A method according to claim 8 wherein said introducing step comprises introducing into tissue of the living subject a probe having thereon a sensor at the tip of said probe.

11. Apparatus for removing a tissue specimen from a living subject comprising:

a biopsy probe;

a perfusion sensor mounted on said biopsy probe for interrogating tissue within a zone surrounding said sensor when said biopsy probe is introduced into tissue of a living subject;

a sensor for monitoring baseline tissue temperature;

means for computing perfusion values as a function of data from said perfusion sensor and said baseline tissue temperature monitoring sensor;

means on said probe for withdrawing tissue from said zone interrogated by said sensor when computed perfusion values are within a biologically significant range.

12. Apparatus for removing a perfused biopsy specimen from a site in a living subject comprising:

a probe having thereon a perfusion sensor defining an effective interrogation zone and a specimen collector located adjacent said perfusion sensor so that said collector is within the effective interrogation zone of said probe;

means for monitoring tissue perfusion n the effective interrogation zone; and means for monitoring baseline temperature and compensating for the effect of baseline temperature fluctuations on perfusion values; wherein said specimen collector is operable to withdraw tissue from the effective interrogation zone when perfusion values are within a biologically significant range.

13. Apparatus for removing a biopsy specimen comprising:

a tissue probe;

means on said probe for introducing thermal energy into tissue and detecting the transport of thermal energy in a volume of tissue adjacent said probe; and a tissue specimen extractor located on said probe to be at least partially within said volume of tissue when in use.

14. Apparatus according to claim 13 wherein said introducing means comprises a sensor on said probe for introducing thermal energy into tissue and detecting the transport of thermal energy, said apparatus further comprising:

a second sensor on said probe for monitoring baseline temperature fluctuations; and a data processor for quantifying tissue blood flow as a function of the output of the first said sensor and said second sensor.

15. Apparatus for removing a biopsy specimen comprising:

a sensor for monitoring the baseline temperature of tissue;

a thermistor for heating tissue above the baseline temperature at a location from which a biopsy specimen is to be removed;

means for determining perfusion at the site of said thermistor as a function of data from said sensor and said thermistor; and means for removing a biopsy specimen from said location when perfusion is within a biologically significant range.

16. Apparatus according to claim 15 wherein said thermistor is adjacent or within said biopsy removing means so that the perfusion value calculated is indicative of the perfusion value at the location from which the biopsy specimen is removed.

* * * * *